United States Patent
McAlpine et al.

(10) Patent No.: US 9,502,638 B2
(45) Date of Patent: Nov. 22, 2016

(54) METHOD OF MANUFACTURING FLEXIBLE PIEZOELECTRIC STRUCTURES

(75) Inventors: Michael C. McAlpine, Lawrenceville, NJ (US); Yi Qi, Plainsboro, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 652 days.

(21) Appl. No.: 13/566,738

(22) Filed: Aug. 3, 2012

(65) Prior Publication Data

US 2012/0312456 A1 Dec. 13, 2012

Related U.S. Application Data (62) Division of application No. 12/727,798, filed on Mar. 19, 2010, now abandoned.

(Continued)

(51) Int. Cl.

| | |
|---|---|
| H01L 41/314 | (2013.01) |
| H01L 21/762 | (2006.01) |
| H01L 41/09 | (2006.01) |
| H01L 41/08 | (2006.01) |
| H01L 41/053 | (2006.01) |
| A61L 31/16 | (2006.01) |
| A61K 51/12 | (2006.01) |
| A61B 5/0408 | (2006.01) |

(52) U.S. Cl.
CPC ......... *H01L 41/314* (2013.01); *H01L 41/0533* (2013.01); *H01L 41/0805* (2013.01); *H01L 41/0986* (2013.01); *A61B 5/0408* (2013.01); *A61K 51/1282* (2013.01); *A61L 31/16* (2013.01); *H01L 21/76251* (2013.01); *H01L 21/76259* (2013.01); *Y10T 29/42* (2015.01); *Y10T 29/49124* (2015.01)

(58) Field of Classification Search
CPC ............... H01L 41/053; H01L 41/0805; H01L 41/0986; H01L 41/314; H01L 21/76251; H01L 21/76259; Y10T 49/42; Y10T 29/49124; A61L 5/1282; A61L 51/1282; A61B 5/0408
See application file for complete search history.

(56) References Cited

U.S. PATENT DOCUMENTS

| | | | | |
|---|---|---|---|---|
| 5,539,965 | A | * | 7/1996 | Safari et al. ............ Y10T 29/42 |
| 5,614,246 | A | * | 3/1997 | Mund .................. A61B 5/0408 427/2.12 |

(Continued)

FOREIGN PATENT DOCUMENTS

JP 2006041049 A * 2/2006

OTHER PUBLICATIONS

Hans Jaffe. "Piezoelectric Ceramics." J. Am. Ceram. Soc., pp. 41,494-498 (1958).

(Continued)

*Primary Examiner* — A. Dexter Tugbang
(74) *Attorney, Agent, or Firm* — Meagher Emanuel Laks Goldberg & Liao, LLP (57) ABSTRACT

A method of making a flexible piezoelectric structure is disclosed. A piezoelectric film is deposited by film deposition on a planar substrate. A biocompatible flexible substrate is contacted with the piezoelectric film. The piezoelectric film and biocompatible flexible substrate are separated from the planar substrate, and the piezoelectric film remaining is attached to the biocompatible flexible substrate.

14 Claims, 5 Drawing Sheets

Related U.S. Application Data (60) Provisional application No. 61/258,943, filed on Nov. 6, 2009, provisional application No. 61/259,304, filed on Nov. 9, 2009.

(56) References Cited

U.S. PATENT DOCUMENTS

| | | | | |
|---|---|---|---|---|
| 6,254,552 | B1* | 7/2001 | Lewis et al. | A61K 5/1282 |
| 6,629,341 | B2* | 10/2003 | Wilkie et al. | H01L 41/0986 |
| 7,244,443 | B2* | 7/2007 | Pacetti | A61L 31/16 |
| 2004/0164650 | A1* | 8/2004 | Xu | H01L 41/314 310/328 |
| 2004/0221447 | A1* | 11/2004 | Ishii | Y10T 29/49124 29/830 |
| 2004/0238866 | A1* | 12/2004 | Iwashita et al. | H01L 41/314 |
| 2006/0156542 | A1* | 7/2006 | Matsuda | Y10T 29/49124 |
| 2007/0096591 | A1* | 5/2007 | Fujii | Y10T 29/42 |
| 2008/0075927 | A1* | 3/2008 | Sakashita | H01L 21/76251 428/172 |
| 2008/0135162 | A1* | 6/2008 | Sakashita | H01L 41/314 |

OTHER PUBLICATIONS

E. Hausler, et al., "Implantable Physiological Power Supply with PVDF Film," Ferroelectrics, 60, pp. 277-282 (1984).
Ryoichi Takayama and Yoshihiro Tomita, "Preparation of epitaxial Pb(ZrxTi1−x)O3 thin films and their crystallographic, pyroelectric, and ferroelectric properties," J. Appl. Phys., 65, pp. 1666-1670 (1989).
Takeo Furukawa and Naoya Seo, "Electrostriction as the Origin of Piezoelectricity in Ferroelectric Polymers," Jpn. J. Appl. Phys., 29(4), pp. 675-680 (1990).
K. Lefki and G. J. M. Dormans, "Measurement of piezoelectric coefficients of ferroelectric thin films," J. Appl. Phys., 76, pp. 1764-1767 (1994).
Jie-Fang Li, et al., "Polarization switching mechanisms and electromechanical properties of La-modified lead zirconate titanate ceramics," J. Mater. Res., 10, pp. 926-938 (1995).
A. L. Kholkin, et al., "Interferometric measurements of electric field-induced displacements in piezoelectric thin films," Rev. Sci. Instr., 67, pp. 1935-1941 (1996).
Thad Starner, "Human-powered wearable computing," IBM Syst. J., 35(3 and 4), pp. 618-629 (1996).
J. C. Lotters, et al., "The mechanical properties of the rubber elastic polymer polydimethylsiloxane for sensor applications," J. Micromech. Microeng., 7, pp. 145-147 (1997).
Xiang-Dong Chen et al., "0-3 Piezoelectric composite film with high d33 coefficient," Sens. Act. A, 65, pp. 194-196 (1998).
J.F. Shepard, et al., "The wafer flexure technique for the determination of the transverse piezoelectric coefficient (d31) of PZT thin films," Sens. Act. A, 71, pp. 133-138 (1998).
Joseph F. Shepard. Jr.. et al., "Characterization and aging response of the d31 piezoelectric coefficient of lead zirconate titanate thin films," J. Appl. Phys., 85, pp. 6711-6716 (1999).
Nathan S. Shenck and Joseph A. Paradiso, "Energy Scavenging with Shoe-Mounted Piezoelectrics." IEEE Micro 21, pp. 30-42 (2001).
E. Venkatragavaraj, et al., "Piezoelectric properties of ferroelectric PZT-polymer composites," J. Phys. D Appl. Phys., 34, pp. 487-492(2001).
S. Dunn and R.W. Whatmore, "Substrate effects on domain structures of PZT 30/70 sol-gel films via PiezoAFM," J. Eur. Ceram. Soc., 22, pp. 825-833 (2002).
Anita M. Flynn and Seth R. Sanders, "Fundamental Limits on Energy Transfer and Circuit Considerations for Piezoelectric Transformers," IEEE T. Power Electr., 17, pp. 8-14 (2002).
Sergei V. Kalin in and Dawn A. Bonnell, "Imaging mechanism of piezoresponse force microscopy of ferroelectric surfaces," Phys. Rev. B, 65, pp. 125408-125418 (2002).
S. Dunn, "Determination of Cross Sectional Variation of Ferroelectric Properties for Thin Film (Ca. 500 nm) PZT (30/70) via PFM," Integr. Ferroelectr., 59, pp. 1505-1512 (2003).
X.Y. Zhang et al., "Synthesis and Piezoresponse of Highly Ordered Pb(Zr0.53Ti0.47)O3 Nanowire Arrays," Appl. Phys. Lett., 85(18), pp. 4190-4192 (2004).
Min-Hua Zhao, et al., "Piezoelectric Characterization of Individual Zinc Oxide Nanobelt Probed by Piezoresponse Force Microscope," Nano Lett., 4(4), pp. 587-590 (2004).
Angus I. Kingon and Sudarsan Srinivasan, "Lead zirconate titanate thin films directly on copper electrodes for ferroelectric, dielectric and piezoelectric applications," Nat. Mater., 4, pp. 233-237 (2005).
Joseph A. Paradiso and Thad Starner, "Energy Scavenging for Mobile and Wireless Electronics," IEEE Pervas. Comput., 4, pp. 18-27 (2005).
Jong-Hyun Ahn. et al., "Heterogeneous Three-Dimensional Electronics by Use of Printed Semiconductor Nanomaterials," Science, 314, pp. 1754-1757 (2006).
Michael C. McAlpine, et al., "Highly Ordered Nanowire Arrays on Plastic Substrates for Ultrasensitive Flexible Chemical Sensors," Nat. Mater., 6, pp. 379-384 (2007).
S. Srinivasan, et al., "Piezoelectric/ultrananocrystalline diamond heterostructures for high-performance multifunctional micro/nanoelectromechanical systems," Appl. Phys. Lett., 90, pp. 134101-1-134101-3 (2007).
Rusen Yang, et al., "Power generation with laterally packaged piezoelectric fine wires," Nat. Nanotechnol., 4, pp. 34-39 (2009).

* cited by examiner

METHOD OF MANUFACTURING FLEXIBLE PIEZOELECTRIC STRUCTURES

CROSS-REFERENCE TO PRIOR FILED APPLICATIONS

This application is a divisional of U.S. patent application Ser. No. 12/727,798 filed Mar. 19, 2010. This application also claims the benefit of U.S. Provisional Application No. 61/258,943, filed on Nov. 6, 2009 and U.S. Provisional Application No. 61/259,304, filed on Nov. 9, 2009, all of which are incorporated by reference as if fully set forth.

UNITED STATES GOVERNMENT RIGHTS

This invention was made with government support under Grant No. 2008-1218103-000 awarded by the Central Intelligence Agency. The government has certain rights in this invention.

FIELD OF INVENTION

This application is directed to flexible piezoelectric structures and a method for making the structures.

BACKGROUND

Stretchable, biocompatible rubbers may yield novel implantable or wearable energy harvesting systems. As one example, decreasing power requirements for mobile electronic devices open the possibility of charging such devices by continuously extracting otherwise wasted energy from the environment. Such charging could be done with or without additional energy supplied by a battery.

Another attractive possibility is that of utilizing work produced by the human body via everyday activities, such as breathing or walking. The heel strike during walking is a particularly rich source of energy, with 67 watts of power available from a brisk walker. Harvesting even 1-5% of that power would be sufficient to run many body-worn devices such as mobile phones. Similarly, it has been shown that lung motion by breathing can generate up to 1 W of power. If this power were harvested into charging a pacemaker battery, for example, it may increase the time required between battery replacement surgeries for patients.

Crystalline piezoelectric materials are promising materials for electromechanical energy conversion technologies. These materials become electrically polarized when subjected to a mechanical stress, and conversely experience a strain in response to an applied electric field, the strain being in proportion to the strength of that field. Single-crystal perovskites, such as lead zirconate titanate (PZT), are an exceptionally efficient class of energy conversion materials. Indeed, conversion of mechanical to electrical energy with efficiencies above 80% has been demonstrated using PZT piezoelectric cantilevers operated near resonance.

Epitaxial growth of such crystalline materials depends on the use of rigid, inorganic host substrates, as well as high temperature deposition processes. For example, rf sputtering at 600° C. has been shown to yield single-crystal films of PZT over large areas with excellent compositional control when deposited on MgO or $SrTiO_3$ substrates. However, next-generation applications, such as wearable energy harvesting systems, may require the piezoelectric materials to be flexible, lightweight, and biocompatible. The flexible piezoelectric polymer polyvinylidene difluoride (PVDF) has been used for applications such as shoe-sole power generators and implantable breath harvesting.

SUMMARY OF THE INVENTION

A flexible piezoelectric structure and a method of making the structure are disclosed. A piezoelectric film having a relatively high piezoelectric coefficient is attached to a flexible substrate. The piezoelectric film is fabricated on a different substrate and transferred to the flexible substrate by contact.

DETAILED DESCRIPTION OF THE INVENTION

Piezoelectric polymers, such as PVDF, suffer a number of drawbacks. The piezoelectric coefficient $d_{33}$ for the organic polymer PVDF, 26 picoCoulombs/Newton (pC/N), is almost ten times smaller than for inorganic PZT, which may exceed 250 pC/N. PZT-PVDF composites can show high performance, but are known to degrade rapidly in air. Piezoelectric crystalline materials, such as PZT, represent a particularly interesting subset of smart materials which function as sensors, actuators, and energy converters. Yet, the crystallization of these materials generally requires relatively high temperatures for maximally efficient performance, rendering them incompatible with temperature-sensitive plastics and rubbers.

The difficulties described above may be overcome with a device structure and a process for fabricating that structure disclosed here. The process is scalable in area for transferring crystalline piezoelectric films with relatively high piezoelectric coefficients, such as PZT, from host substrates onto flexible rubbers over macroscopic areas. The resulting structure includes a material of relatively high piezoelectric coefficient on a flexible substrate. Such structures may enable a host of novel applications. The disclosed piezoelectric structure is flexible, light in weight, and may be made biocompatible. It may therefore be suitable for providing electrical energy for wearable and/or implantable devices. The described structure has relatively higher mechanical-electric coupling, and is therefore more efficient at energy conversion than polymer type piezoelectric materials such as PVDF or composite type piezoelectric materials like a PZT/polymer composite.

The method and device structures described here may be used for making wearable or implantable energy harvesting devices such as shoe-sole power generators or implantable devices harvesting energy from motions of breathing. The device structures may replace batteries or augment them with a portable charging source. The device structures may also be laminated against vibrating machines to harvest otherwise wasted energy by mechanical motors or internal combustion engines.

The method and device structures described here may provide continuous scavenging of energy from the environment in which they reside. Advantages of this type of energy harvester may include a high degree of portability, flexibility, stretchability, and low weight. Other advantages may include biocompatibility and higher resistance to degradation due to air, water, heat, and other environmental factors. Still other advantages include relative ease and low cost of fabrication compared to bulk piezoelectric crystals.

The structure described here may also be used in an opposite fashion, in which the structure undergoes mechanical motion in response to applied electrical energy. The structure could thus be used to convert electrical energy to mechanical energy. For example, the structure could be part of a wing that flaps in response to an electrical signal, thereby enabling an object to fly.

The method and device structures disclosed here include at least one thin film of piezoelectric material on a flexible substrate. The structure may include a patterned piezoelectric film on a flexible substrate. The piezoelectric film may be patterned as a plurality of ribbons or belts having a non-circular cross-section. Such patterns will be referred to hereafter as ribbons. Such ribbons are distinct from other structures in which the piezoelectric material is in the form of "wires" or "fibers" having a circular cross section.

Figure 1:
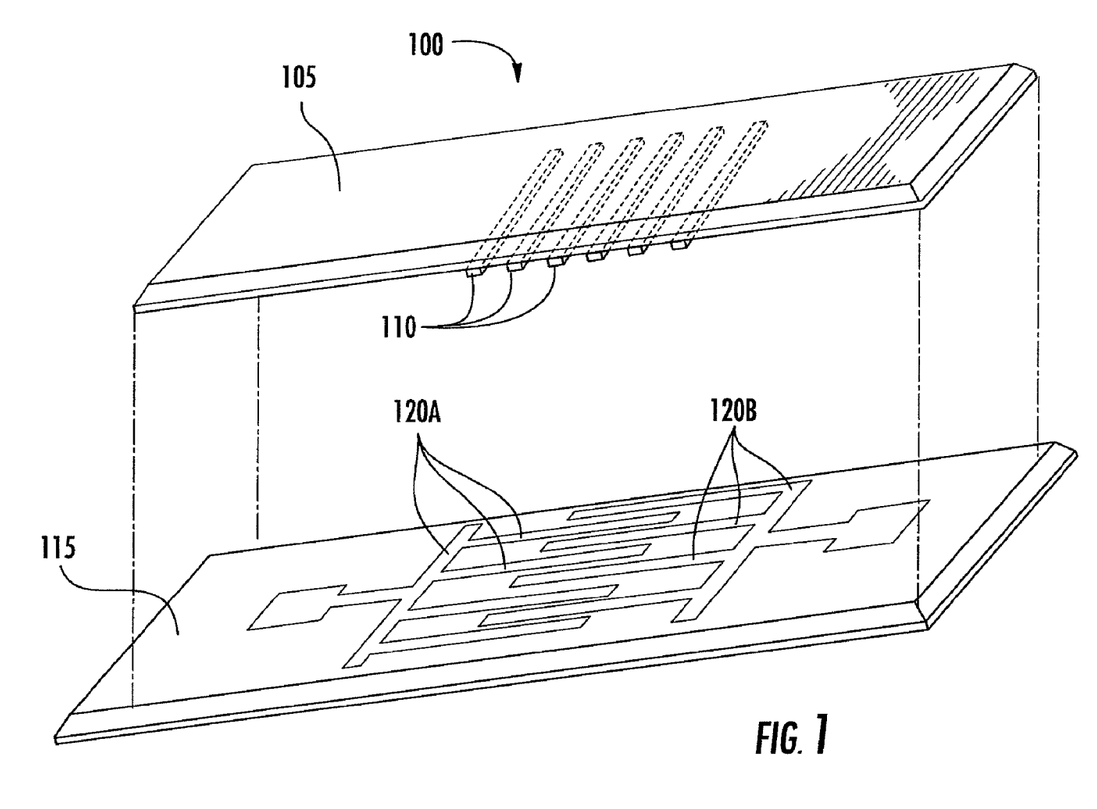
FIG. 1 shows an embodiment of a flexible piezoelectric structure.

FIG. 1 shows an embodiment of a device structure 100, not intended to be limiting. Device structure 100 includes a patterned piezoelectric film 110 attached to a first flexible substrate 105. In this embodiment piezoelectric film 110 is patterned as a plurality of ribbons on a surface of first flexible substrate 105. These ribbons 110 have a non-circular cross-section and differ from wires or fibers as explained above.

Piezoelectric film 110 may contain a non-polymeric material, a non-crystalline material, a partially crystalline material, a polycrystalline material, or a crystalline material. Piezoelectric film 110 may have a piezoelectric coefficient significantly greater than that of PVDF and of other piezoelectric organic polymers. Piezoelectric film 110 may contain an inorganic material such as a perovskite. Suitable materials for use as piezoelectric film 110 include, but are not limited to, PZT, ZnO, Quartz, $LiNbO_3$, $SrTiO_3$, $BaTiO_3$, lead zirconate, or lead titanate, in any combination.

Figure 4:
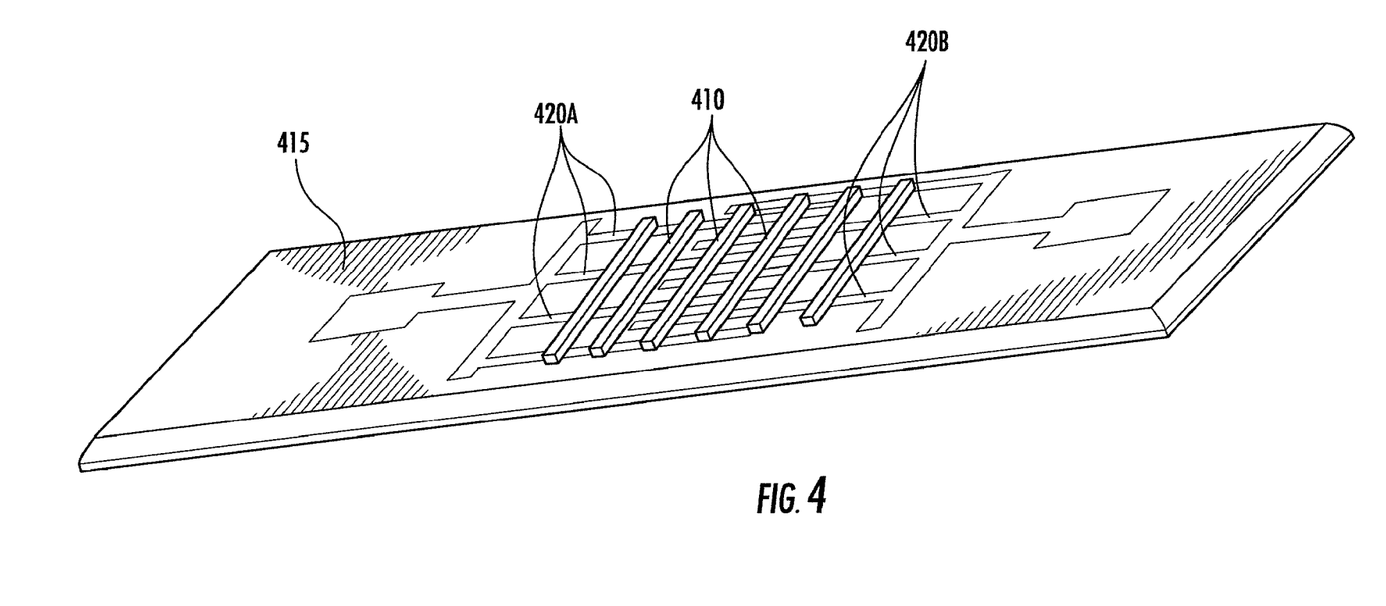
FIG. 4 shows an embodiment of a flexible piezoelectric structure with an alternate electrode configuration.
Figure 5:
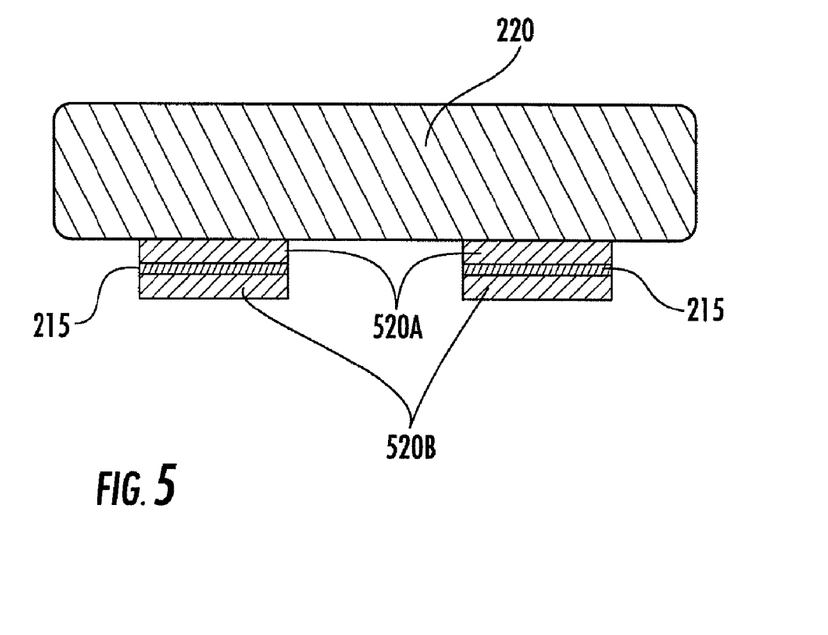
FIG. 5 shows an embodiment of a flexible piezoelectric structure with another alternate electrode configuration.

Still referring to the embodiment shown in FIG. 1, a second flexible substrate 115 is shown. Two electrodes 120A and 120B are attached to a side of second flexible substrate 115 facing a surface of first flexible substrate 105 upon which patterned piezoelectric film 110 is situated. First flexible substrate 105 and second flexible substrate 115 may be brought together and bonded to each other, as indicated by the arrows at the right of FIG. 1, forming a single integral structure with first electrode 120A and second electrode 120B in contact with patterned piezoelectric film 110. First electrode 120A and second electrode 120B provide means of making electrical contact with patterned piezoelectric film 110 so that electrical energy produced by the flexing of patterned piezoelectric film 110 may be collected. First electrode 120A and second electrode 120B may be made by depositing a conducting film, such as a metal film, on second flexible substrate 115 and patterning the conducting film using known techniques. In the embodiment shown in FIG. 1, first and second electrodes 120A and 120B are shown as an interdigitated pair, with fingers running perpendicular to the ribbons. Alternative configurations of electrodes can be used, depending, for example, on the type of piezoelectric response exhibited by patterned piezoelectric film 110. In one alternative, two electrodes may make contact respectively on opposite sides of patterned piezoelectric film 110 and/or electrode fingers may run predominantly parallel to the ribbons. FIG. 5 shows a cross section of one such possible configuration. In this configuration piezoelectric ribbons 215 are sandwiched between electrode 520A and electrode 520B. Furthermore, both electrodes 520A and 520B run parallel to piezoelectric ribbons 215. Electrode 520A is in contact with flexible substrate 220. Another alternative electrode configuration is shown in FIG. 4. In this alternative first electrode 420A and second electrode 420B are both in contact with one side of patterned piezoelectric film 410 and are situated between patterned piezoelectric film 410 and flexible substrate 415.

Patterned piezoelectric film 110 may be completely encapsulated by, for example, first flexible substrate 105 and second flexible substrate 115 in FIG. 1. In this way, it may be possible to make a structure which is fully biocompatible even when piezoelectric film 110 contains a toxic material such as lead, as is the case with PZT.

In another alternative, a second patterned piezoelectric material (not shown) may be fabricated either alongside or stacked over patterned piezoelectric film 110. With multiple fabrications of patterned piezoelectric material alongside each other, structures of arbitrary large area can be produced, as explained below.

Suitable materials for first flexible substrate 105 and second flexible substrate 115 include, but are not limited to, polydimethylsiloxane (PDMS), polyethylene terephthalate (PET), polyether ether ketone (PEEK), a polyimide such as Kapton®, or a polyester such as Mylar®, all in any combination.

FIGS. 2A-2F show an embodiment of a process for fabricating a flexible piezoelectric structure. FIGS. 2A-2F and the following descriptions do not include some steps, such as cleaning and heat treatments, which are known to a person of ordinary skill in the art. The following description of a process embodiment is an example and is not to be construed as limiting.

Figure 2A:
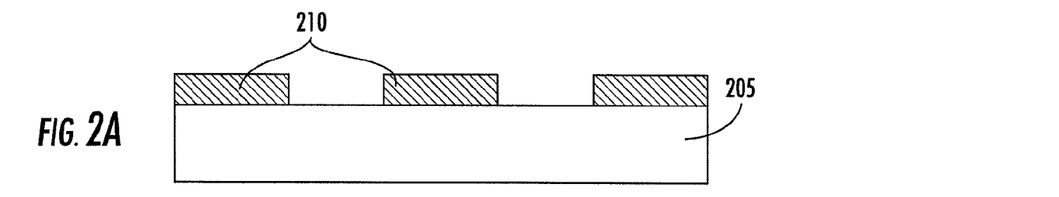
FIGS. 2A-2F show an embodiment of a method of fabricating a flexible piezoelectric structure.

Starting in FIG. 2A a patterned sacrificial layer 210 is formed on a substrate 205. One suitable material for substrate 205 is MgO. Patterned sacrificial layer 210 may be formed using photoresist. The photoresist may be spin-coated onto substrate 205 and patterned using photolithography. In this embodiment the sacrificial layer is given a negative pattern—that is, the pattern of the sacrificial layer is designed to be the negative complement of a desired final pattern of a piezoelectric film.

Figure 2B:
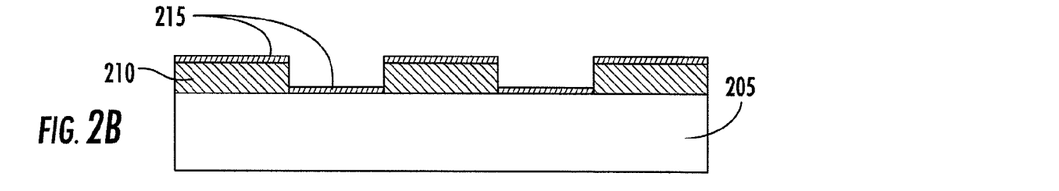

As shown in FIG. 2B, a piezoelectric film 215 is formed over patterned sacrificial layer 210. Piezoelectric film 215 may be formed by film deposition techniques including, but not limited to, sputtering, including rf sputtering; hydrothermal deposition; chemical vapor deposition (CVD), including metal-organic CVD; sol-gel deposition; laser ablation; pulsed laser deposition; or molecular beam epitaxy. Film deposition may be followed by annealing of the film which may increase the film piezoelectric coefficients. Piezoelectric film 215 may be a non-polymeric, non-crystalline, partially crystalline, polycrystalline, or a crystalline material. Piezoelectric film 215 may have a piezoelectric coefficient significantly greater than that of PVDF and of other piezoelectric organic polymers. Piezoelectric film 215 may be an inorganic material such as a perovskite. Suitable materials for use as piezoelectric film 215 include, but are not limited to, PZT, ZnO, Quartz, $LiNbO_3$, $SrTiO_3$, $BaTiO_3$, lead zirconate, or lead titanate, in any combination. Piezoelectric film 215 may have a thickness ranging from a few hundred nanometers to several micrometers.

Figure 2C:
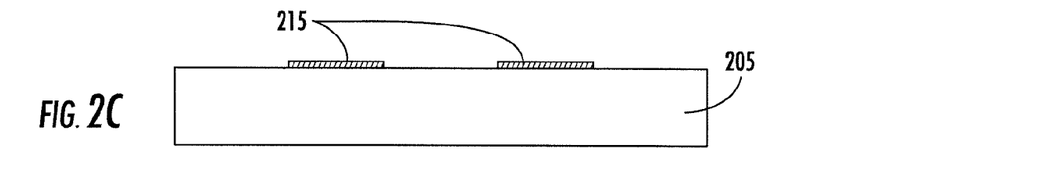

As shown in FIG. 2C, patterned sacrificial layer 210 may then be removed, taking with it undesired portions of piezoelectric film 215. Removal of patterned sacrificial layer 210 may be done in a liquid solution. This is often referred to as a lift-off process.

Figure 2D:
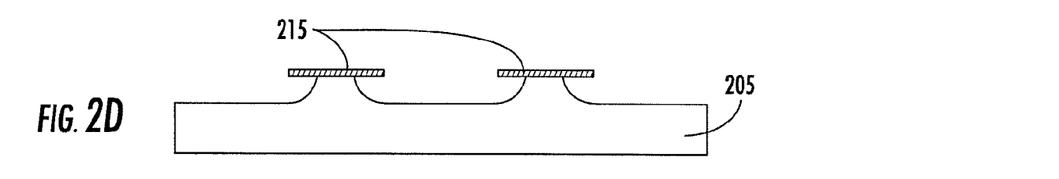

As shown in FIG. 2D, substrate 205 is undercut in order to reduce an area of contact between substrate 205 and piezoelectric film 215. This may be accomplished, for example, using a wet etch to partially dissolve substrate 205. This will have the effect of reducing the overall thickness of substrate 205 while undercutting, as shown by comparing FIGS. 2C and 2D.

Figure 2E:
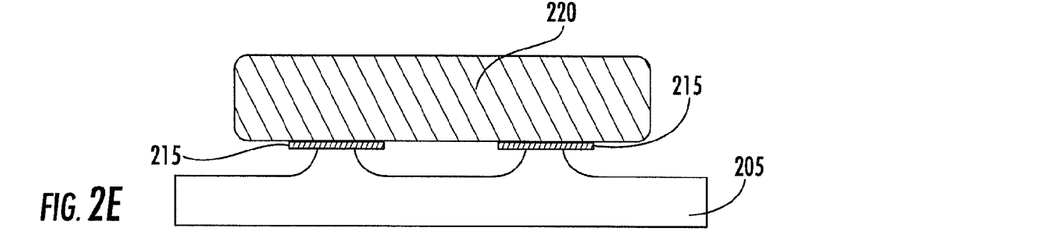

As shown in FIG. 2E a flexible substrate 220 may be brought into conformal contact with patterned piezoelectric film 215. Suitable materials for flexible substrate 220 include, but are not limited to, polydimethylsiloxane (PDMS), polyethylene terephthalate (PET), polyether ether ketone (PEEK), a polyimide such as Kapton®, or a polyester such as Mylar® in any combination.

Figure 2F:
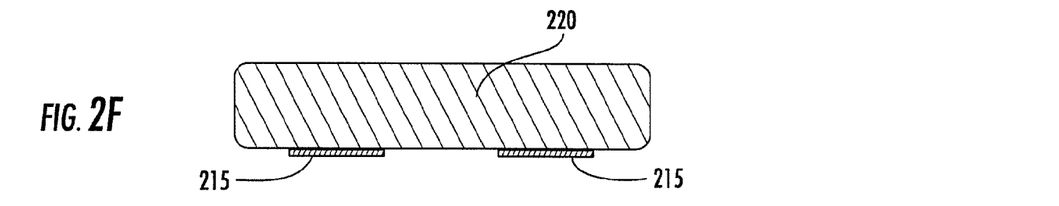

Flexible substrate 220 may then be separated from substrate 205, resulting in the structure shown in FIG. 2F. If adhesive forces between flexible substrate 220 and patterned piezoelectric film 215 exceed adhesive forces between patterned piezoelectric film 215 and substrate 205, then patterned piezoelectric film 215 may be transferred intact to flexible substrate 220. The undercutting of substrate 205 shown in FIG. 2D enhances the likelihood of a successful transfer.

In the embodiment shown in FIGS. 2A-2F piezoelectric film 215 is shown patterned into ribbons with non-circular cross-sections, as distinct from wires or fibers having circular cross-sections, as described above. In an alternative embodiment, the piezoelectric film may be unpatterned. An unpatterned film may produce greater electrical power for a given mechanical stress than a patterned film, at least because the unpatterned film has greater volume.

The process of FIGS. 2A-2F is scalable to any area. The steps of FIGS. 2A-2E may be repeated with the same flexible substrate 220 to transfer a second patterned piezoelectric film to a region of flexible substrate 220 alongside first patterned piezoelectric film 215. In similar manner, an arbitrary area of flexible substrate 220 may be covered with patterned piezoelectric film.

In a similar manner, multiple patterned piezoelectric films may be stacked one on top of another on a single flexible substrate 220 by repeating the process of FIGS. 2A-2F.

Once at least one patterned piezoelectric film 215 has been transferred to flexible substrate 205, electrodes may be attached to patterned piezoelectric film 215, resulting in a final structure such as that shown in FIG. 1 and discussed above.

Figure 3A:
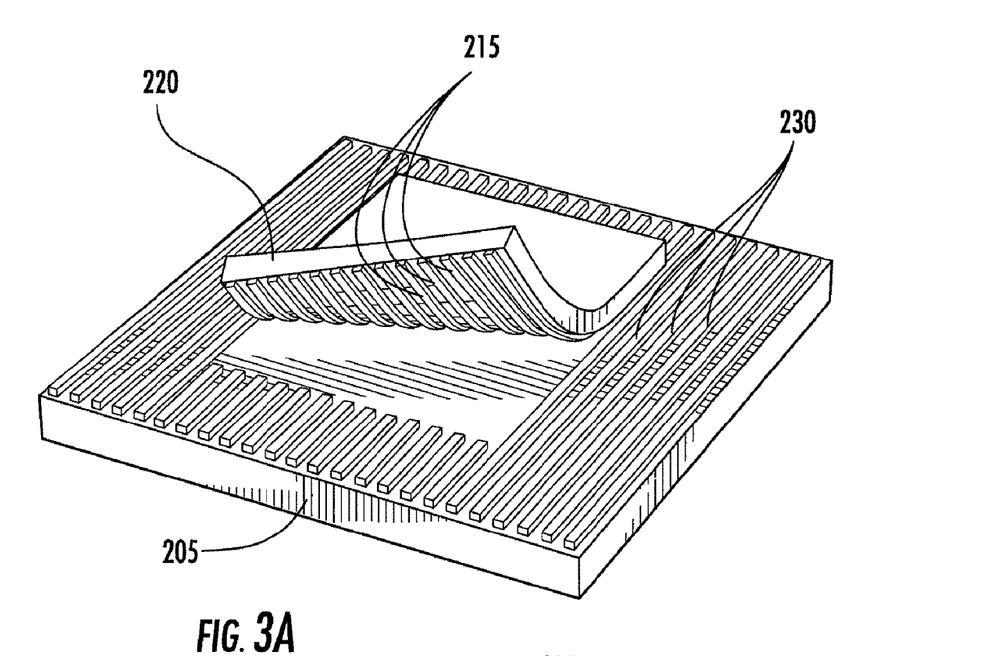
FIGS. 3A and 3B show respectively one step in a method of fabricating a flexible piezoelectric structure and the resulting structure component.
Figure 3B:
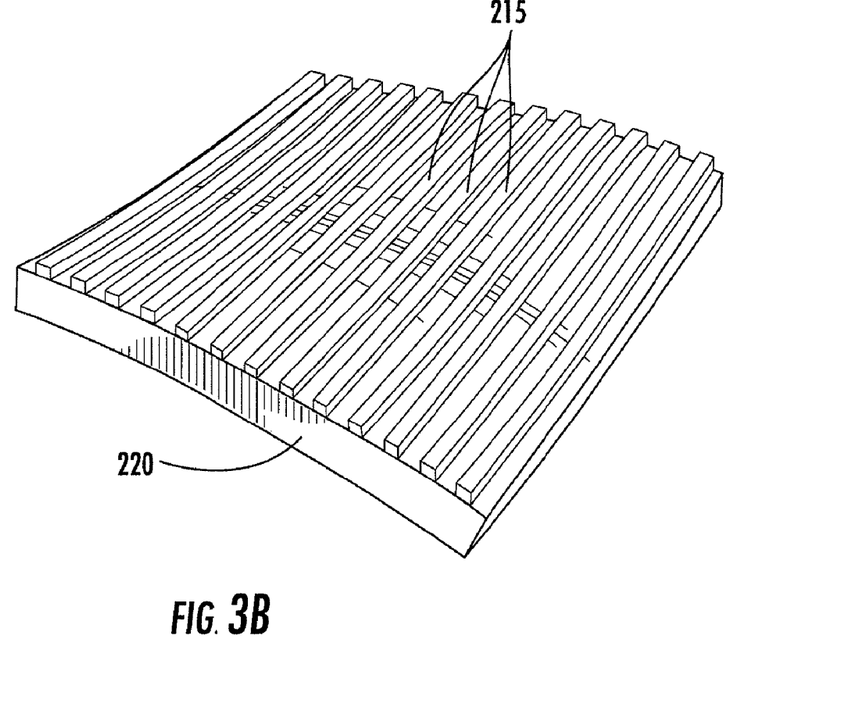

FIG. 3A shows a perspective view of the transfer of patterned piezoelectric film 215 to flexible substrate 220 and FIG. 3B shows a perspective view of flexible substrate 220 with completely transferred patterned piezoelectric film 215. All guide numbers correspond to features shown in FIG. 2.

Obtaining highly crystalline piezoelectric materials such as PZT may be important to performance as studies have indicated an inherent reduction in the piezoelectric coefficient of thin PZT films due to internal defects. Likewise, in the case of PZT, generating ribbons with a stoichiometric composition near the morphotropic phase boundary of PZT ($Pb[Zr_xTi_{1-x}]O_3$ with x=0.52) is needed for maximum piezoelectric response and poling efficiency. Poling refers to processes in which the electric polarization in a region of a piezoelectric material is permanently altered by the application of an electric field for a limited time.

Example structures were fabricated using PZT films patterned in multiple ribbons similar to the example shown in FIG. 3B. Compositional and structural characterization of the PZT film from which the ribbons were patterned was done. X-ray diffraction (XRD) and scanning electron microscopy (SEM) were used to characterize the structure of the PZT film. XRD data shows clear peaks corresponding to the perovskite structure (100) and (200) faces, indicating a tendency toward epitaxial growth with a c-axis perpendicular to the film surface, while the perovskite (111) and pyrochlore peaks are relatively minor. Indeed, the SEM image shows no obvious surface texture. Energy dispersive spectroscopy (EDS) was used to characterize the composition of the PZT film. A comparison of the EDS curves for an annealed sample against a standard sample (52/48, Zr/Ti) showed peak intensities that were nearly identical for each element, indicating insignificant lead and zirconium loss during growth and post-annealing.

An important parameter for characterizing fundamental piezoelectric performance is d, the piezoelectric charge constant as discussed in IEEE/ANSI 176 IEEE Standard on Piezoelectricity (1987), which is incorporated herein by reference. This value represents the polarization generated per unit of mechanical stress applied to a piezoelectric material, or, conversely, the mechanical strain experienced by a piezoelectric material per unit of electric field applied. The piezoelectric charge coefficient is a tensor, with components $d_{ij}$, where i indicates the direction of polarization generated in the material when the electric field is zero (or the direction of the applied field strength), and j is the direction of the applied stress (or the induced strain). Obtaining high d values is essential for energy harvesting applications, as the energy conversion efficiency (electromechanical coupling factor, k) of piezoelectric materials scales proportionally with d.

One of the piezoelectric constants is $d_{31}$, in the transverse operation mode. This mode has been used in applications such as energy generation from piezoelectric shoe implants. Using a wafer flexure method, $d_{31}$ was determined to be 49 pC/N for an as-annealed sample. This spontaneous polarization of the film confirms the tendency of the c-axis of the film to be the out of plane direction. Significantly, this value increased to $d_{31}$=79 pC/N when the sample was poled at −100 kV/cm for 14 hours. These values are in agreement with the best reported data for PZT films grown by sputtering and are a factor of 3-4 times higher than typical values for PVDF ($d_{31}$, PVDF=20-25 pC/N).

Another useful quantity for characterizing the performance of a piezoelectric material is $d_{33}$, the induced polarization per unit stress applied in the longitudinal (poling) direction. To characterize the performance of PZT ribbons, $d_{33}$ measurements were conducted before and after transfer printing to a flexible substrate, as described above. A PZT film with a Pt bottom contact electrode on an MgO substrate was analyzed using Piezoresponse Force Microscopy (PFM). A value of $d_{33}$=82 pC/N was measured. The film was subsequently continuously scanned with a 10 V DC bias voltage (100 kV/cm) over a small area (100 n m.sup.2) for 30 min to pole the sample; d33 was found to increase to as high as 173 pC/N after poling. This thin film value is comparable to values for organometallic chemical vapor deposited PZT films.

Direct $d_{33}$ measurements were performed on PZT ribbons after transfer to PDMS. To apply an AC bias voltage, the PDMS was doped with 13% wt carbon black to render it conducting. For the as-transferred sample, $d_{33}$ was determined to be 40 pC/N, while with poling was found to yield $d_{33}$=79 pC/N. This value represents a 3-fold improvement over previously measured values for ZnO nanobelts on rigid substrates ($d_{33,ZnO\ Nanobelt}$=27 pC/N).

The electromechanical energy conversion metrics disclosed here are among the highest reported on a flexible medium. The excellent performance of the piezo-ribbon assemblies coupled with stretchable, biocompatible rubber may enable a host of novel applications.

While several embodiments have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present embodiments. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings herein is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, the embodiments disclosed may be practiced otherwise than as specifically described and claimed. The present embodiments are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present embodiments.

What is claimed is:

1. A method for fabricating a biocompatible flexible piezoelectric structure, comprising:
    depositing a first piezoelectric film by film deposition on a planar substrate;
    patterning the first piezoelectric film;
    contacting a biocompatible flexible substrate with the first piezoelectric film; and
    separating the first piezoelectric film and biocompatible flexible substrate from the planar substrate, the first piezoelectric film remaining attached to the biocompatible flexible substrate,
    wherein at least a portion of the piezoelectric film is deposited directly on the planar substrate with a patterned layer.

2. The method of claim 1, wherein the patterning comprises patterning the first piezoelectric film into ribbons having a non-circular cross-section.

3. The method of claim 2, further comprising fabricating electrode fingers running parallel to the ribbons.

4. The method of claim 2, further comprising fabricating electrode fingers running perpendicular to the ribbons.

5. The method of claim 1, wherein depositing comprises at least one of sputtering, radio-frequency sputtering, hydrothermal deposition, chemical vapor deposition (CVD), metal-organic CVD, sol-gel deposition, laser ablation, pulsed laser deposition, or molecular beam epitaxy.

6. The method of claim 1, wherein the first piezoelectric film comprises an inorganic material.

7. The method of claim 1, wherein the first piezoelectric film comprises at least one of a non-polymeric material, a non-crystalline material, a partially crystalline material, a polycrystalline material, or a crystalline material.

8. The method of claim 1, wherein the first piezoelectric film comprises a material having a piezoelectric coefficient exceeding 10 picoCoulombs/Newton.

9. The method of claim 1, further comprising encapsulating the first piezoelectric film with a second flexible substrate.

10. The method of claim 1, further comprising fabricating first and second electrodes in contact with the first piezoelectric film.

11. The method of claim 1, wherein the first and second electrodes are both fabricated in contact with one side of the first piezoelectric film.

12. The method of claim 1, wherein the first and second electrodes are respectively fabricated in contact with opposite sides of the first piezoelectric film.

13. The method of claim 1, wherein the flexible substrate comprises at least one of: polydimethylsiloxane (PDMS), polyethylene terephthalate (PET), polyether ether ketone (PEEK), a polyimide, or a polyester.

14. The method of claim 1, further comprising fabricating at least one additional piezoelectric film stacked over the first piezoelectric film.

* * * * *